US00PP28172P3

(12) United States Plant Patent
Byrne et al.

(10) Patent No.: US PP28,172 P3
(45) Date of Patent: Jul. 11, 2017

(54) PEACH TREE NAMED 'ROYAL ZEST TWO'

(50) Latin Name: *Prunus persica*
Varietal Denomination: Royal Zest Two

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 15 days.

(21) Appl. No.: 14/544,506

(22) Filed: Jan. 13, 2015

(65) Prior Publication Data

US 2016/0205843 P1 Jul. 14, 2016

(51) Int. Cl.
*A01H 5/08* (2006.01)

(52) U.S. Cl.
USPC ..... Plt./197

(58) Field of Classification Search
USPC ..... Plt./197, 198
See application file for complete search history.

(56) References Cited

U.S. PATENT DOCUMENTS

PP7,290 P 8/1990 Zaiger et al.

OTHER PUBLICATIONS

New Peach Varieties Available in January for Home Gardens Across Texas, http://today.agrilife.org/2013/12/30/new-peach-varieties-available-in-january-for-home-gardens-across-texas/, Dec. 30, 2013.*

"Royal and Golden Zest Peaches," http://aggie-horticulture.tamu.edu/fruit-nut/files/2010/10/Royal-Golden-Zest-Peaches-one-Pager-Feb-8-2013.pdf, Feb. 8, 2013.*

The Brooks and Olmo Register of Fruit and Nut Varieties, 3rd Ed., American Society of Horticultural Science Press, Alexandria, VA, 1997.

Brooks, R. M. 1958. Double Delight, Earligold, and June Gold peaches. Fruit Var. J. 3:22.

Okie, W. R. 1993. 'Goldprince' and 'Scarletpearl' peaches. HortScience 28:231.

Rouse, R. and W. Sherman. 1989. 'TropicBeauty': a low-chilling peach for subtropical climates. HortScience 24:165-166.

* cited by examiner

*Primary Examiner* — Anne Grunberg
(74) *Attorney, Agent, or Firm* — Ramey & Schwaller, LLP

(57) ABSTRACT

Disclosed is a new variety of *Prunus persica* named 'ROYAL ZEST TWO'. This new variety, which requires approximately 500 chilling units of dormancy, is considered to be a peach tree of early mid-season maturity, which produces yellow fleshed fruit that are firm, attractively colored, and suitable for the fresh fruit market.

5 Drawing Sheets

BACKGROUND OF THE INVENTION

Field of the Invention

This invention relates to peach trees and, more specifically, to peach trees referred to as a variety of *Prunus persica* named 'Royal Zest Two'. 'Royal Zest Two', which requires approximately 500 chilling units of dormancy, produces a high quality, firm semifreestone peach that matures in early mid-season.

SUMMARY OF THE INVENTION

The 'Royal Zest Two' peach is characterized as to novelty and is otherwise noteworthy by producing fruit that ripens in the early mid-season; is considered high quality; and which is firm and has an attractive coloration. In this regard, the present variety of peach tree bears fruit that are ripe for commercial harvesting and shipment in late May to early June, when the fruit is grown in the medium chill zone of Texas. 'Royal Zest Two' ripens about 7 days earlier than the 'June Gold' peach, a non-patented variety (Brooks, 1958. Fruit Var. Journal 3:22).

Origin of the Variety

The present peach tree was the result of an ongoing Stone Fruit Breeding Program of Texas A & M University, College Station, Brazos County, Tex. To this end, both controlled crosses are made each year to produce seedling populations from which improved plants are selected.

'Royal Zest Two' (RZ2, TX4D165) originated from a cross between the yellow-fleshed California peach 'Rich Lady' (Zaiger et al., 1990. U.S. Plant Pat. No. 7,290) and the early ripening, medium chill peach, 'Victor'. UPOV PBR PRUNU PER grant #25391). 'Victor' was released by Texas A&M University for use in Spain and is a seedling from the cross between the low chill, yellow-fleshed, mid-season cultivar 'Tropic Beauty' (not patented) and the early ripening, yellow-fleshed, medium chill peach 'Goldprince' (not patented). 'Tropic Beauty' was jointly released by the University of Florida and Texas A&M University (Rouse and Sherman, 1989. HortScience 24:165-166) and is derived from a cross between an unreleased Florida selection Fla3-2 (K6E121 open pollinated) and the non-patented peach cultivar 'Flordaprince' (Fla2-7 (non-patented)×'Maravilha' (non-patented)) (Okie, 1998). 'Goldprince' (non-patented)

was released by the USDA breeding program in Byron, Ga. (Okie, 1993. HortScience 28:231) and is derived from a cross between 'Loring' (not patented, Okie, 1998) and the unreleased Georgia selection FV3-257. Resulting seed from this cross were planted in 1998 at the Texas A & M University Horticultural Farm in College Station, Tex. 'ROYAL ZEST TWO' was marked for subsequent observation and noted as having exceptional characteristics. Two-year and older trees of the variety were subsequently evaluated during the 2005 through 2011 fruit growing seasons in both California (Clovis) and Texas (Terrell, Fairfield and College Station).

The new variety 'Royal Zest Two' differs from its yellow fleshed, high chill, peach female parent 'Rich Lady' in that it requires less chilling hours to break dormancy, blooms 7-8 days earlier, ripens 6-10 days earlier and generally has a rounder shape in the medium chill zone of Texas.

The new variety 'Royal Zest Two' differs from 'Victor', its yellow fleshed peach pollen parent, in that it requires more chilling accumulation to break dormancy, blooms 8-10 days later, and ripens 17-19 days later.

Asexual Reproduction of the Variety

'Royal Zest Two' was bud grafted onto virus-free Nemaguard ("The Brooks and Olmo Register of Fruit and Nut Varieties," 3rd Ed., American Society of Horticultural Science Press, Alexandria, Va., 1997, unpatented) peach rootstock in June 2000 at the nursery site in Oakdale, Calif. The variety was subsequently planted at the experimental orchard in the central portion of the San Joaquin Valley, near Fowler, Fresno County, Calif. and in three sites in Texas (College Station, Fairfield and Terrell). Fruit from the resulting propagation has been evaluated during the period from 2005 to 2011 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographic drawings and depicts the plant by the best possible color representation using color photography, wherein.

BOTANICAL DESCRIPTION OF THE VARIETY

Figure 1:
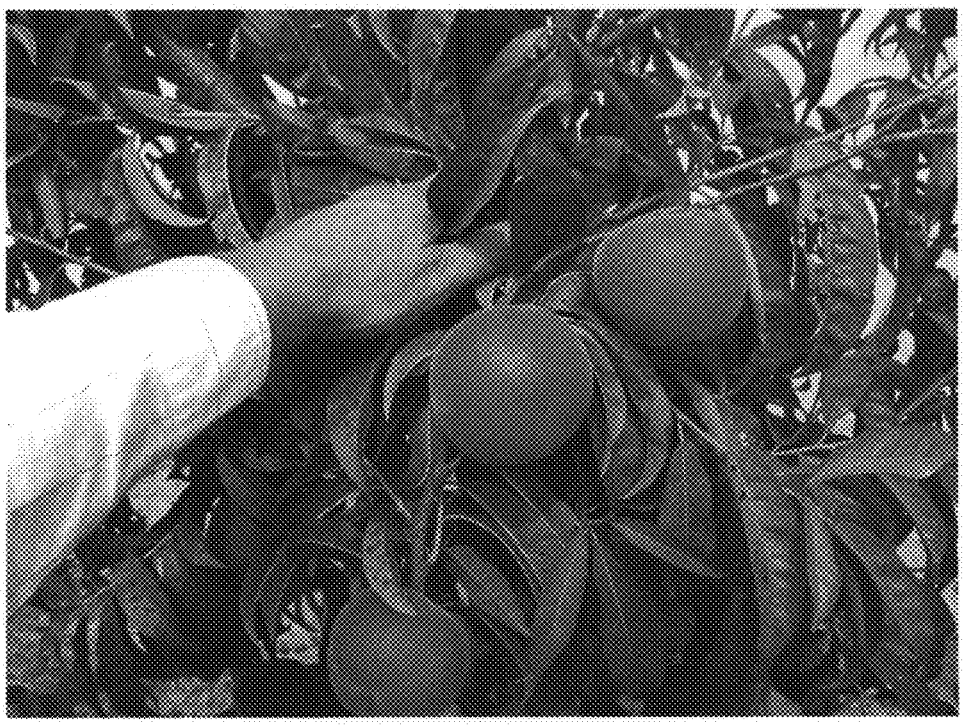
FIG. 1 A color photograph of a characteristic twig bearing typical leaves and several mature fruit showing their external coloration sufficiently matured for harvesting and shipment of 'Royal Zest Two' as grown in Clovis, Calif.
Figure 2:
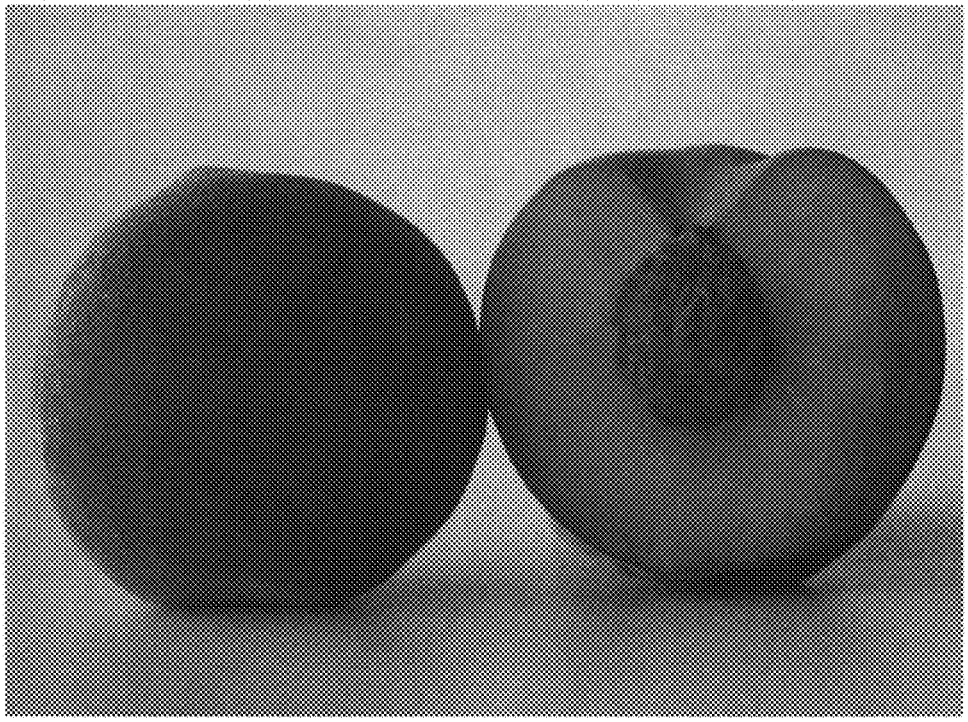
FIG. 2. Color picture showing the flesh and skin color and fruit shape of 'Royal Zest Two' produced in the medium chill zone of Texas (Fairfield).
Figure 3:
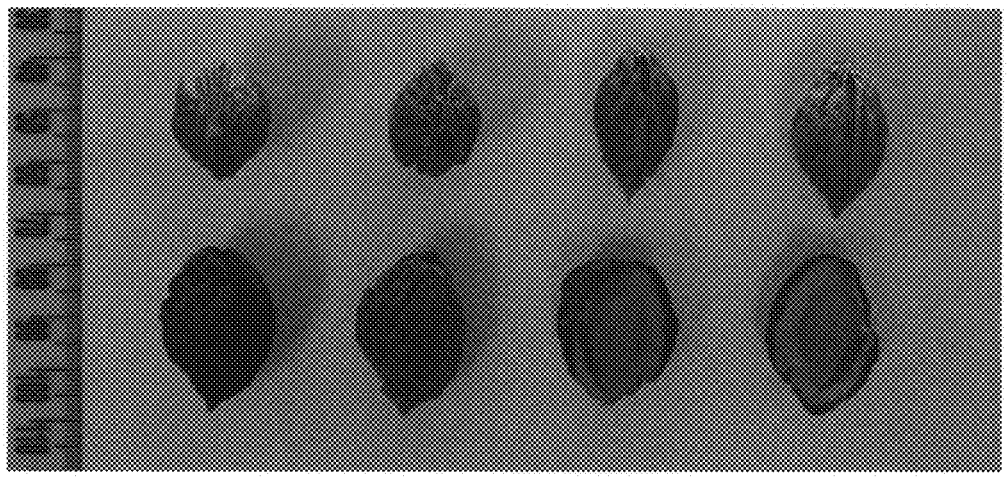
FIG. 3. Color photograph of the endocarp of 'Royal Zest Two'. The ruler is demarcated in millimeters.
Figure 4:
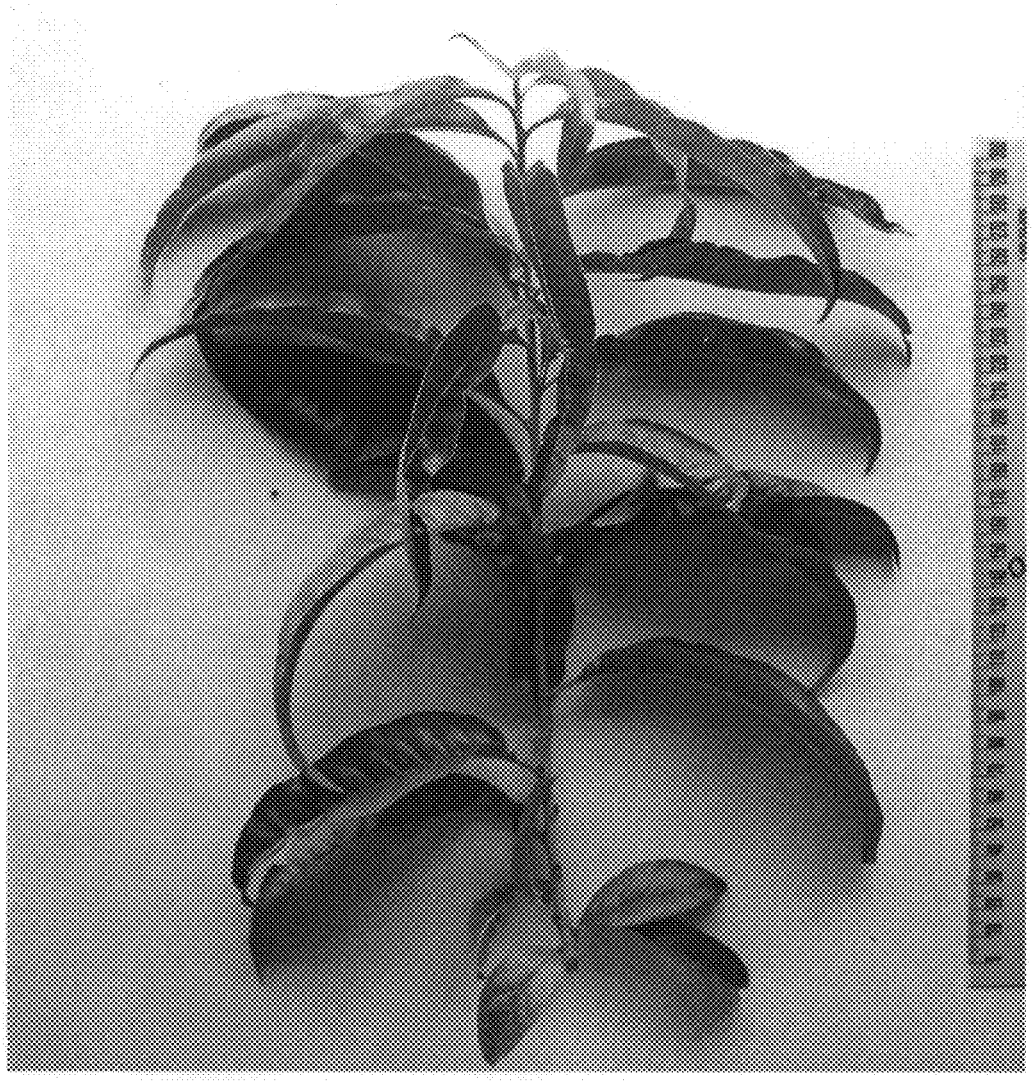
FIG. 4. A shoot showing the leaves of the 'Royal Zest Two' peach. The ruler is demarcated in millimeters.
Figure 5:
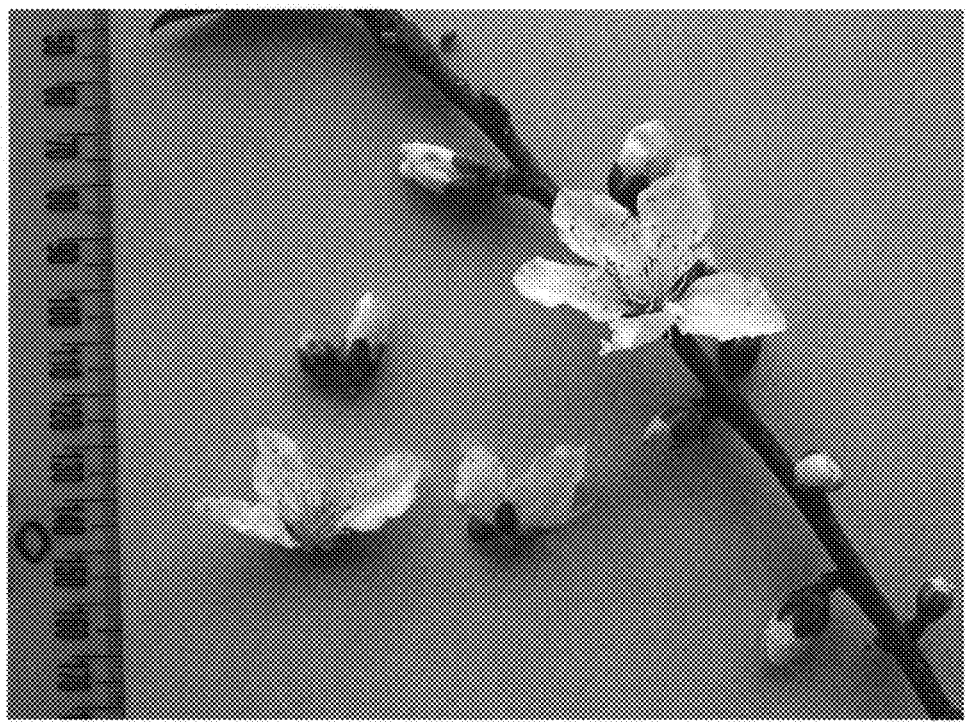
FIG. 5. The showy flowers of 'Royal Zest Two'. The ruler is in millimeters.

Referring more specifically to the pomological details of this new and distinct variety of peach tree, the following has been observed under the ecological conditions prevailing at the experimental orchards in the medium chill zone of Texas (Fairfield and College Station). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars ripening in the early season of maturity.

*Height*.—7.5 feet (2.29 m) on five-year old trees pruned to an open center training system.

*Width*.—7 feet (2.13 m) on five-year old trees pruned to an open center training system.

*Vigor*.—High.

*Density*.—Medium to high.

*Productivity*.—Productive.

*Shape*.—The trees are vigorous with the typical semi-spreading growth habit similar to 'TexKing' (Byrne and Bacon, 2004, U.S. Plant Pat. No. 14,627), 'TexPrince' (Byrne and Bacon 2004, U.S. Plant Pat. No. 14,629), and 'TexRoyal' (Byrne and Bacon, 1991, unpatented).

*Current season growth*.—The current season growth for the new variety was approximately 3.0 to 3.3 feet (0.91-1.12 m).

*Regularity of bearing*.—Regular, and considered hardy under typical conditions in the medium chill zone of Texas and in the central San Joaquin Valley of California.

Trunk:

*Size*.—Approximately 11.5 cm in diameter and 41.3 cm in circumference when measured at a distance of approximately 30.5 cm above the soil level, at the end of the 2012 growing season on a five-year old tree.

*Bark texture*.—Considered moderately rough with numerous folds of papery scarf-like skin being present.

*Bark coloration*.—Variable, colors present are 164B-C and 166A of the Greyed-Orange Group, 183A-C and 187D of the Greyed-Purple Group, 199B-D of the Grey-Brown Group and N200D of the Brown Group.

Branches:

*Size*.—Considered medium for the variety.

*Thickness*.—Average (about 7.2 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 4.0 to 9.0 mm in width and were approximately 1 mm in height.

*Current season shoots*.—Surface texture — Substantially glabrous.

*Internode length*.—Approximately 29 to 36 mm as measured in the middle of a current season stem.

*Color of mature branches*.—The predominant colors are 166B-C and 175A-B of the Greyed-Orange Group, 198D of the Greyed-Green Group, N200D of the Brown Group and 202D of the Black Group.

*Current season shoots*.—Color — Varies from a medium/light green to a yellow green (Approximately Yellow-Green Group N144A&D and 145A-D) with some reddish-brown coloration appearing on exposed surface of the shoots (Approximately Greyed-Orange Group 173A-B and 174B).

*Type of bearing*.—Long shoots only.

*Spur length*.—Not applicable.

*Vegetative bud size*.—Generally 1.0-1.5 mm in length on the mid portion of a summer shoot.

*Vegetative bud shape of apex*.—Acute.

*Position of vegetative bud in relation to one year old shoot*.—Adpressed.

Leaves:

*Size*.—Considered medium for the species. Leaf measurements have been taken from vigorous upright current season growth approximately at mid-shoot.

*Leaf length*.—Approximately 165 to 176 mm.

*Leaf width*.—Approximately 37 to 46 mm.

*Leaf thickness*.—Less than 1 mm.

*Leaf form*.—Lanceolate.

*Leaf tip form*.—Acuminate. The tip occasionally appears flexed downwards and slightly twisted laterally.

*Leaf upper surface color*.—Green, approximately 137A of the Green Group.

*Leaf lower surface color*.—Green, approximately 137C of the Green Group.

*Leaf mid-vein color*.—Green, approximately 138D and 142D of the Green Group.

*Leaf margins*.—Form — Considered crenate/crenulate. Uniformity — Considered generally uniform.

*Leaf petioles*.—Size — Considered medium to medium long. Length — Approximately 9 to 10 mm. Thickness — Approximately 1.5 to 2 mm. Color — Pale green (Yellow Green Group 144B-D).

*Leaf glands*.—Size — Approximately 1 mm or less in height and width. Number — Generally 2-3 per leaf. Type — Globose. Color — Brown (N200A Brown Group). Position — predominantly on the base of the leaf blade.

*Leaf stipules*.—Size — Medium for species. Length — Approximately 9 to 11 mm. Form — Lanceolate. Color — Light green (Yellow-Green 144B-C) with reddish brown tips (Greyed-Orange Groups 164B-C and 165B) when young. The stipules are considered to be early deciduous. Ratio of wood (leaf) buds to flowering buds — 1 to 2 flower buds per vegetative bud.

Flowers:

*Floral buds*.—General — The floral buds are considered to be medium in size, conic in form, and slightly appressed relative to the bearing shoot. Color — The bud scales are gray-brown, (approximately Greyed-Purple Group 187A, Brown Group 200A-B and N200A). The buds are considered hardy under typical central San Joaquin Valley, Calif. climatic conditions. Length — Approximately 4 to 7 mm. Blooming Type — Considered medium early in relation to other peach cultivars commonly growing in the medium chill zone of Texas (Fairfield). Date of full bloom was between February 22nd and March 10th during the period between 2006 and 2011 with an average bloom date of March 1st about 10 days before the 'June Gold' peach blooms. Flower fertility — self fertile. Flower Type — Showy. Flower Size — Flower diameter at full bloom is approximately 23 to 27 mm. Bloom Quantity — Considered abundant. Flower Bud Frequency — Normally 1 per node on samples taken from College Station, Tex.

*Petal size*.—General — Considered medium for the species. Width — Approximately 10 to 12 mm. Length — Approximately 15 to 17 mm. Petal Form — Broadly ovate. Petal Count — Nearly always 5. Petal Color — Light pink when young (Red-Purple Group 62D, 65C-D, 69A-B and 73D). Flower Arrangement of petals — touching at the base of the petals.

*Petal claw*.—Form — The claw is considered present. Length — Approximately 1 to 1.5 mm. Width — Approximately 1 mm or less. Petal Margins — Generally considered smooth. Petal Apex — Generally — The petal apices appear slightly domed.

*Flower pedicel*.—Length — Considered medium with an average length of approximately 2 to 3 mm. Thickness — Considered average, approximately 1 mm. Color — A medium green (Yellow-Green Group 144D and 145A-B).

*Floral nectaries*.—Color — Orange (Yellow-Orange Group 21A-B, 23A-B and Orange Group 24A).

*Calyx*.—Surface Texture — Generally glabrous. Color — Highly variable from green near pedicel attachment to red-brown (approximately Yellow-Green Group 144D and 145A-B and Red-Purple Group 60A, Greyed-Red Group 181A, Greyed-Purple Group 183A-B and 185A).

*Sepals*.—Surface Texture — The surface has a short, fine, wooly and a gray-colored texture. Size — Average, and ovate in form. Color — Highly variable from dull red to red and maroon with green (approximately Red-Purple Group 59A-B, 60A-B, Green Group 138B, Yellow-Green Group 144A-B, Greyed-Red Group 178A-B, Greyed-Purple Group 183A-C and Greyed-Green Group 191A).

*Anthers*.—General — Average in size for the species. Color — Golden yellow (approximately Yellow-Orange Group 15A, 17A-B and 21A-C). Position with respect to pistil — generally at the same height or higher. Position with respect to petals — anthers do not protrude when the flower is at the pink bud stage. Pollen Production — Pollen is abundant. Tree is self-fertile.

*Filaments*.—Size — Variable in length, approximately 12 to 15 mm, with the filaments generally longer than or equal to the pistil. Color — White (approximately White Group 155A-D).

*Pistil*.—General — Average in size, but slightly equal to or shorter, relative to the general anther height, overall. Length — Approximately 17 to 18 mm, including the ovary. Color — Considered a light yellow with pale green when young (approximately Green-Yellow Group 17D, Yellow Group 2D, 4C-D, Yellow-Green Group 145C, 150C-D and 154B-D). Surface texture — The variety has a long, pale green (approximately 150C of the Yellow-Green) to whitish green (range from Green White Group 157A to 157D) pubescent pistil.

Fruit:

*Maturity when described*.—The present variety of fruit is described, as it would be found in its firm ripe condition at full commercial maturity. Under the ecological conditions prevailing in the medium chill zone of Texas, it would be ripe in late May to Early June. The average ripe date at College Station is May 23rd and in Fairfield would be June 5th.

*Size.*—General — Medium large to large for the season and considered uniform.

*Average cheek diameter.*—Approximately 58 to 63 mm.

*Average suture diameter.*—Approximately 61 to 67 mm.

*Average axial diameter.*—Approximately 52 to 55 mm.

*Fruit form.*—Generally quite oblate in its lateral aspect. Occasionally the fruit exhibits less symmetry when comparing the suture height with the line opposite the suture. The fruit is generally uniform in symmetry when viewed from the apical aspect.

*Fruit suture.*—Generally, the suture appears as a thin line that extends from the base to the apex, and appears slightly deeper at the apex, forming a shallow basin at the apical point. No apparent callusing or stitching exists along the suture line. Fruit suture depth — at midpoint it has a depth of 0-2 mm. Color — The suture normally is the same color as the underlying blush which is a reddish-orange color (Greyed Orange Group 171A). Ventral Surface — Form — Considered uniform.

*Stem cavity.*—Size — Considered large for the species. Width — Approximately 29 to 36 mm. Length — Approximately 18 to 22 mm. Depth — Approximately 15 to 16 mm. Fruit Base — Generally considered flat. Fruit Apex — Generally considered variable between flat and round.

*Fruit stem.*—Generally — Considered medium in length, approximately 10 mm. Thickness — Approximately 4 mm. Color — Generally a medium green (approximately Yellow Green Group 141C).

*Fruit skin.*—Generally considered medium or average in thickness. Surface Texture — The variety has very short, thin pubescence. Skin Acidity — Considered neutral. Tenacious to Flesh — Yes. Tendency to Crack — Not observed. Skin Color — Generally — Variable, with approximately 40-90% of the fruit surface covered with an attractive red/purple blush. Down — Short. Blush Color — The blush color is generally more prevailing apically. This dark red/purple blush (Red-Purple Group 59A-B and Purple Group N77A) has many degrees of shading and blending occurring between the stated colorations. Skin Ground Color — The skin ground is a pale to medium yellow (approximately Yellow Group 4B).

*Flesh color.*—Generally considered variable from light yellow near the stone (approximately Yellow Group 5C) to a dark red as it nears the skin (Orange-Red Group N34A).

*Flesh fibers.*—Present, numerous and lightly colored. These fibers are present throughout the flesh.

*Stone cavity flesh color.*—Generally considered a medium to light yellow (Yellow Group 5D).

*Flesh texture.*—Generally, the flesh is considered firm and fine at commercial maturity.

*Ripening.*—Generally the fruit of the present variety ripens evenly.

*Flavor.*—Considered sweet with an acid flavor.

*Soluble solids.*—Range from 10-15 Brix. The average Brix is 12.3.

*Titratable acidity.*—Generally between 0.7-1.15 Eq $H^+$/1000 mL of juice depending on the ripeness of the fruit sampled.

*Aroma.*—Pleasant and reasonably abundant.

*Eating.*—Generally considered very good to excellent.

Stone:

*Attachment.*—Considered semifreestone at commercial maturity.

*Stone size.*—Generally considered medium to medium-small relative to the ratio of stone to fruit size. Length — Approximately 28 to 30 mm. Width — Approximately 18 to 23 mm. Thickness — Approximately 16 to 17 mm. Fibers — Generally a few short fibers are attached in variable areas along the surface of the stone. Stone Form — Generally the stone is considered to be elliptical. Stone Base — The stone is considered medium. Apex — Shape — The stone apex is considered narrow to medium. Stone Shape — The stone shape is considered ovoid to elongated.

*Stone surface.*—Surface Texture — Some moderate grooving is apparent over the apical shoulders. Surface pitting has numerous single pits and rosettes of pits. Ridges — Numerous fine ridges are present basally, and converge towards the base of the stone. Ventral Edge — Width — Considered small to medium-small. Dorsal Edge — Shape — Grooved with relatively smooth edges. The dorsal edge is moderately eroded over the apical shoulder. Stone Color — The color of the dry stone is light to brown (approximately Greyed-Yellow Group 161C-D and Greyed-Orange Groups 164A-B and 165B-D). The color of the inside surface of the endocarp is primarily Greyed-Orange N167C. Tendency to Split — Splitting is relatively uncommon.

*Kernel.*—The kernel fills the endocarp at harvest and measures approximately 5-6 mm in thickness, 9-10 mm in width, and 15-17 mm in length. When dried the shriveled kernels measure approximately 3-4 mm in thickness, 9-10 mm in width, and 14-15 mm in length. The colors of the dried kernels are approximately Greyed-Orange Group 165A-B. The kernel is not viable if stratified under moist cool conditions.

*Use.*—The subject variety, 'ROYAL ZEST TWO', is considered to be a peach tree of early mid-season maturity, which produces fruit which are very firm, attractively colored, and which are useful for both local and long distance shipping.

*Keeping quality.*—Good.

*Resistance to insects and disease.*—No particular susceptibilities were noted.

*Shipping quality.*—Average.

Although the new variety of peach tree possesses the described characteristics when grown under the ecological conditions prevailing in the medium chill zone of Texas in College Station and Fairfield, it will be understood that variations of the usual magnitude and characteristics incident to the changes in growing conditions, fertilization, pruning, and pest control are to be expected.

REFERENCES

Brooks, R. M. 1958. Double Delight, Earligold, and June Gold peaches. Fruit Var. J. 3:22.

Brooks, R. M. and H. P. Olmo. 1997. Register of New Fruit and Nut Varieties. 3rd Edition. American Society of Horticultural Science Press, Alexandria, Va.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

Okie, W. R. 1993. 'Goldprince' and 'Scarletpearl' peaches. HortScience 28:231.

Okie, W. R. 1998. Handbook of peach and nectarine varieties, USDA, ARS, Agric. Handbook No. 714.

Rouse, R. and W. Sherman. 1989. 'TropicBeauty': a low-chilling peach for subtropical climates. HortScience 24:165-166.

Sherman, W. B. and P. M. Lyrene. 1992. Flordaprince peach. Fruit Var. J. 46:66-67.

Zaiger, C. F., G. N. Zaiger, L. M. Gardner, and G. G. Zaiger. 1990. Peach tree 'Rich Lady'. U.S. Plant Pat. No. 7,290. Aug. 7, 1990.

We claim:

1. A new and distinct *Prunus persica* tree, substantially as illustrated and described herein.

* * * * *